United States Patent [19]

Diamond

[11] 4,054,957
[45] Oct. 25, 1977

[54] USER-FORMED URINATION TROUGH

[76] Inventor: Harry Diamond, 340 Verona Ave., Elizabeth, N.J. 07208

[21] Appl. No.: 697,561

[22] Filed: June 18, 1976

[51] Int. Cl.$^2$ .................... E03D 13/00; B65G 11/02; B67C 11/02

[52] U.S. Cl. .................... 4/110; 128/132 R; 128/292; 141/337; 193/2 R; 294/55

[58] Field of Search ............ 128/132 R, 132 P, 292; 4/110; 2/49 R; 193/25 R, 25 A, 2 R; 141/337, 338; 229/1.5 R, 4.5; 15/257.1; 294/55; 93/84 R

[56] References Cited

U.S. PATENT DOCUMENTS

| 433,882 | 8/1890 | Belding | 193/2 R |
|---|---|---|---|
| 591,953 | 10/1897 | Davenport | 294/55 |
| 762,737 | 6/1904 | Meinecke | 128/292 |
| 1,040,392 | 10/1912 | Ogle et al. | 193/2 R |
| 2,173,344 | 9/1939 | Spanel | 2/49 R |
| 2,855,607 | 10/1958 | Sullivan | 4/110 |
| 2,878,486 | 3/1959 | Bartlett et al. | 4/110 |
| 3,332,547 | 7/1967 | Rowe et al. | 2/49 R |
| 3,364,928 | 1/1968 | Creager et al. | 128/132 D |
| 3,446,325 | 5/1969 | Robbins | 193/25 R |
| 3,579,653 | 5/1971 | Kuhn | 4/110 |

Primary Examiner—Richard E. Aegerter
Assistant Examiner—John W. Shepperd
Attorney, Agent, or Firm—Shapiro and Shapiro

[57] ABSTRACT

An open-top elongated, foldable V-shaped urination trough for use following prostatic surgery to channel urine away from a patient's body and to prevent its discharge onto clothing and skin, has base and tab portions formed from a single sheet of flexible material. The sheet is folded so that the base portions form sidewalls of an elongated trough. The tab portions are bent into engagement with each other to form a finger hold and to define an opening near one end of the trough.

2 Claims, 2 Drawing Figures

USER-FORMED URINATION TROUGH

BACKGROUND OF THE INVENTION

This invention relates to urination apparatus and is more particularly concerned with forming a trough-like device for use following prostatic surgery to channel urine away from a patient's body and to prevent its discharge onto clothing and skin.

A condition commonly encountered following prostatic surgery is an inability of sustain and control a forceful flow of urine. From time to time, the patient finds himself dribbling during efforts to urinate, with a resultant discharge of urine onto clothing and skin. While the dribbling problem usually subsides as the prostate heals, it frequently continues for a time after the patient has returned to work and has resumed the routine of daily life.

SUMMARY OF THE INVENTION

It is accordingly a principal object of the present invention to provide apparatus for facilitating urination.

Another object of the invention is to provide a trough in site for channeling urine away from the body and for preventing its discharge onto clothing and skin.

Still another object is to provide a simple and inexpensive urination apparatus which can be carried inconspicuously.

Briefly stated, urination apparatus embodying the present invention comprise a sheet of material having base portions which are bendable out of a common plane to form an elongated trough, and having tab portions which are bendable into engagement with each other to define an opening at one end of the trough. The base portions preferably include a pair of sidewalls which are connected along a longitudinally extending fold line. The tab portions preferably include a pair of elongated tabs, each of which connects with a separate one of the sidewalls at a location spaced from the fold line. The tab portions are preferably provided with formations to facilitate their being arranged and held in a desired position of engagement.

BRIEF DESCRIPTION OF THE DRAWINGS

The invention will be further described in conjunction with the accompanying drawings, which illustrates a preferred and exemplary embodiment, and wherein.

DETAILED DESCRIPTION OF THE INVENTION

Figure 1:
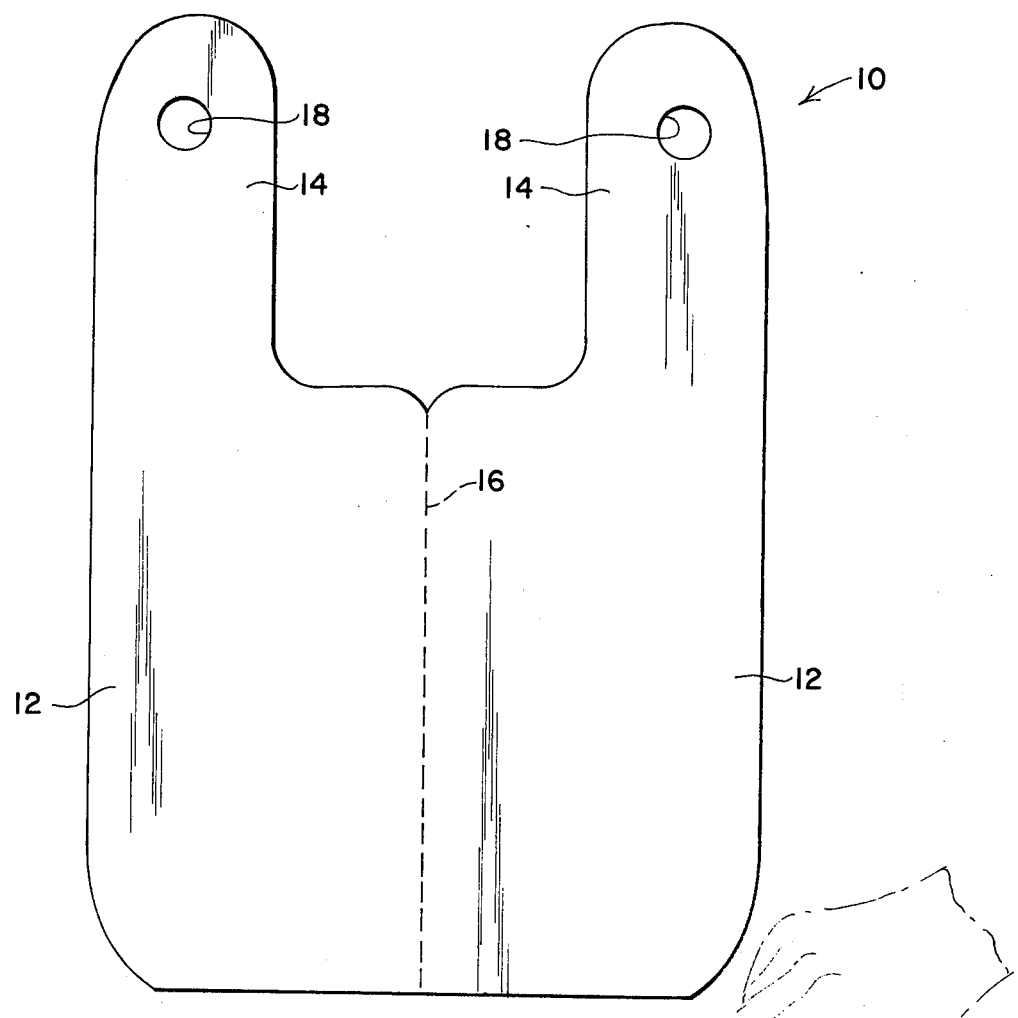
FIG. 1 is a plan view showing the apparatus with all portions lying in a common plane.

Referring to the drawings, and initially to FIG. 1 thereof, a urination apparatus formed from a single sheet of flexible material is indicated generally by the numeral 10. The apparatus 10 includes a pair of elongated base portions 12, and a pair of elongated tab portions 14. A central fold line 16 extends along the juncture of the base portion 12. Holes 18 are formed through the tab portions 14.

The base portion 12 are of substantially rectangular configuration, one being substantially the mirror image of the other. The tab portions 14 join the base portions 12 at locations spaced from the fold line 16, and extend parallel to the fold line when the portions 12, 14 are coplanar. When the apparatus 10 is folded along the fold line 16 such that the base and tab portions 12, 14, are, respectively, superposed, the base and tab portions 12, 14 congruently overlie each other. While folded in this manner, the apparatus 10 can be carried inconspicuously in the pocket of a shirt or suit coat.

Figure 2:
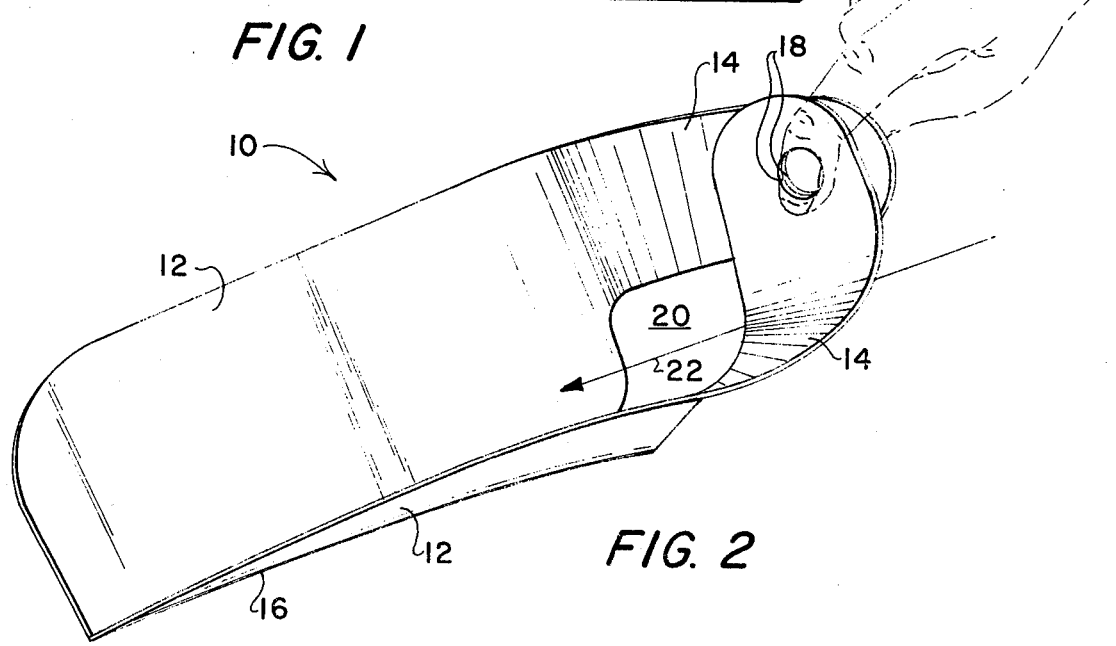
FIG. 2 is a perspective view of the apparatus as folded to form a trough-like device.

In FIG. 2, the apparatus 10 is shown folded along the line 16 such that the base portions 12 are angulated upwardly away from each other to form opposite sidewalls of an open-top trough of generally V-shaped cross-section. The tab portions 14 are bent inwardly and upwardly in a curvilinear manner to bring their free ends into a position of overlapping engagement where the holes 18 are aligned. The engaging tab portions 14 cooperate with ends of the base portions 12 to embrace and define a trough end opening 20. The aligned holes 18 are large enough to receive the finger tips of the user to provide a convenient finger grip for holding the tab portions 14 in proper orientation during use, thereby maintaining the trough shape.

The apparatus 10 is used by inserting ones penis through the opening 20, as indicated by an arrow 22. During urination, the trough defined by the base portions 12 channels urine along a downwardly inclined trajectory for discharge at a location away from ones body. The apparatus 10 prevents urine which dribbles or is not otherwise forcefully ejected from the penis from discharging onto clothing and skin.

The apparatus 10 may be formed from any suitable material such as paper, thin plastic, and the like. It can be formed from durable, washable material and used repeatedly, or can be formed from inexpensive material and disposed of after use.

While a preferred embodiment of the invention has been shown and described, it will be apparent to those skilled in the art that changes can be made in this embodiment without departing from the principles and spirit of the invention, the scope of which is defined in the appended claims.

The invention claimed is:

1. An open-top V-shaped urination trough constituted by a single sheet of flexible material, having a pair of sidewalls extending from a central fold line of said sheet upwardly away from each other, and having a pair of tabs extending from a common end of said walls, respectively, at regions of said walls spaced from said central fold line, each tab being bent to extend upwardly and inwardly of the respective walls into overlapping engagement to define a trough with a hole at one end embraced by said tabs.

2. An open-top urination trough in accordance with claim 1, wherein each of said tabs has a hole therein, the holes in said tabs being aligned and large enough to receive finger tips of a user of the trough gripping the tabs.

* * * * *